United States Patent [19]

Mausner

[11] Patent Number: 5,093,109
[45] Date of Patent: Mar. 3, 1992

[54] COSMETIC COMPOSITION

[75] Inventor: Jack Mausner, New York, N.Y.

[73] Assignee: Chanel, Inc., New York, N.Y.

[21] Appl. No.: 505,015

[22] Filed: Apr. 4, 1990

[51] Int. Cl.$^5$ ............................................... A61K 7/48
[52] U.S. Cl. ........................................ 424/63; 514/783; 424/195.1
[58] Field of Search ................ 424/63, 195.1; 514/783

[56] References Cited

FOREIGN PATENT DOCUMENTS

WO84/03836 10/1984 PCT Int'l Appl. ................. 514/783

Primary Examiner—Thurman K. Page
Assistant Examiner—Susan S. Rueker
Attorney, Agent, or Firm—Charles Berman

[57] ABSTRACT

An emulsified cosmetic composition for treatment of the skin's complexion comprises (a) an anti-aging agent retarding the effects of natural aging on the skin's complexion, including deterioration of the structure and complexion of the skin from free radical activity, (b) a sunscreen retarding the effects on the complexion of the skin from aging of the skin due to sunlight, (c) a preservative, (d) a thickener, (e) an anti-oxidant, and (f) an emulsifier.

18 Claims, No Drawings

COSMETIC COMPOSITION

BACKGROUND

This invention is directed to a cosmetic composition for skin.

With age, the complexion of the skin, namely the color and appearance of the skin, deteriorates. This results in the wrinkled, sagging, reddish, leathery skin of the elderly. With aging, the complexion of the skin and its tone move to the pink/red from the more youthful yellow/pale part of the spectrum. Exposure to sunlight and the destructive effect of free radical activity accelerate the deterioration of the complexion of the skin.

Full or partial recovery of healthy skin color and tone is important for people whose skin's condition has worsened due to aging and/or exposure to sunlight. To achieve such recovery, many people now resort to cosmetic surgery, which involves high costs and the risks of anesthesia and surgery.

Sunscreens have been promoted as anti-aging cosmetic compositions, useful in preventing sun-induced skin damage that accelerates aging. However, sunscreens are not effective against the natural formation of free radicals in the skin nor are they effective against the effects of natural aging on the complexion of the skin. Cosmetic compositions effective against free-radical formation are not useful against the effects of sunlight and do not retard the effects of natural deterioration on the complexion of the skin.

Accordingly, there is a need for a cosmetic product that is effective in retarding the effects of natural aging, aging caused by sunlight, and damage from free-radical activity on the skin's structure and complexion.

SUMMARY

The present invention satisfies this need by providing a product that retards the deleterious effects of natural aging, free radical activity, and sunlight on the complexion of the skin.

The product that accomplishes these results is an emulsified cosmetic composition comprising a water and an oil phase, and dispersed in the water an oil phases (a) an anti-aging agent retarding the effects of natural aging and free radical activity on the skin's complexion, and (b) a sunscreen retarding the effects of aging due to sunlight on the skin's complexion. The emulsified cosmetic composition further comprises (c) a preservative for preventing microbial growth in the composition, (d) a thickener to increase the viscosity of the composition, (e) an antioxidant to prevent rancidity and discoloration of the composition, and (f) an emulsifier for combining the water phase and oil phase ingredients as well as for giving the composition a suitable texture when applied to the skin.

The anti-aging agent is selected from the group consisting of proteins, flavonoid compounds, glycogen, and combination thereof. The proteins can comprise serum proteins and hydrolyzed animal proteins. The flavonoid compounds can be provided by extracts of the plants butcher broom, buckwheat, and passion flower.

The sunscreen can be selected from the group consisting of paraminobenzoic acid derivatives, oxyphenones, benzophenones, titanium dioxide, zinc oxide, cinnamate, and combinations thereof.

The preservatives can be propylene glycol, trisodium EDTA, Phenonip , a preservation complex, and combinations thereof. The preservation complex contains methylparaben, propylparaben, 2-bromo-2-nitropropane-1,3diol, and hexamidine diisethionate. Phenonip is a commercially available preservative and contains phenoxyethanol, methylparaben, ethylparaben, propylparaben, and butylparaben.

The antioxidant can be Tenox II and/or ascorbyl palmitate. Tenox II is a commercial product which contains propylene glycol, butylated hydroxyanisole, propyl gallate, and citric acid.

Preferred thickeners are xanthan gum and carrageenan.

The composition can also contain one or more colorants, such as titanium dioxide.

DESCRIPTION

The present invention provides a cosmetic composition in an emulsified base suitable for treatment of the skin. The new cosmetic composition has the advantage of not forcing a consumer to use multiple products to achieve multiple effects. The inventors have found that it is possible to prepare an emulsified cosmetic composition, containing multiple agents, with multiple effects against the effects of natural and suninduced aging of the skin on the skin's complexion. Applied to the skin, the cosmetic composition's multiple effects are: (a) retarding the effects of natural aging and free radical activity on the structure and complexion of the skin, and (b) retarding the effects of aging by caused by exposure to sunlight on the complexion of the skin. This is particularly advantageous because it makes the present invention markedly superior to compositions that merely apply to the skin a film of rouges, tints, and other coloring agents, or compositions that make the skin temporarily moister.

Surprisingly, tests reveal that the composition serves to restore the complexion to a more youthful appearance. In other words, not only does this composition retard aging, it helps turn back the clock, giving a user a more youthful appearing complexion.

A preferred cosmetic composition embodying the present invention is presented in Table 1. Approximate ranges of ingredients in the composition are also presented in Table 1. These ingredients are dispersed in an emulsified composition by the method of preparation discussed below. "Dispersal" refers to any process by which the ingredients are uniformly distributed in the emulsified base, and includes dissolving, emulsifying, and forming a colloidal suspension. Dispersal involves sufficient mixing until visual inspection of samples reveals an absence of powder or lumps in the composition. Table 2 provides details about the ingredients identified in Table 1 by tradename. Each of the various ingredients will now be discussed.

Anti-aging ingredients

The agents for retarding the effects of natural aging and aging due to free radical activity on the skin's complexion are selected from the group consisting of proteins, flavonoid compounds, glycogen, and combinations thereof. The emulsified composition of the present invention employs a commercial source for the proteins, flavonoid compounds, and glycogen. These ingredients are supplied in various combinations in two products, called Flavoplasmine LS2704 P2 (hereinafter Flavoplasmine) and Iconoderm LS 1054 B (hereinafter Iconoderm), both available from Lab Serobiologiques, Inc., Somerville, New Jersey.

The active ingredients of Flavoplasmine are serum proteins, hydrolyzed animal proteins and flavonoid compounds. The flavonoid compounds within the Flavoplasmine are furnished by butcher broom extract, buckwheat extract, and passion flower extract. The respective weight ratios of these ingredients in Flavoplasmine are presented in Table 2. The Flavoplasmine further contains a monostearatepolyethylene glycol ester of stearic acid (PEG 6-32) serving as an emulsifier, and glycerin functioning as a solvent.

Iconoderm (see Table 2) comprises serum proteins, hydrolyzed animal proteins, and glycogen. Sodium lactate is present for buffering. Iconoderm further contains sodium pyrrolidone carboxylate.

The anti-free radical ingredients of the emulsified cosmetic composition can be selected from the group consisting of derivatives of vitamins C or E, selenium metal compounds, or beta carotene derivatives.

Sunscreens

The agents protecting against aging of the skin's complexion due to sunlight are one or more of the sunscreens identified in Table 3. A satisfactory cosmetic composition comprises octyldimethyl paraminobenzoic acid and benzophenone-3 in the respective concentrations shown in Table 1.

Preservatives

Since the emulsified cosmetic composition is manufactured under clean but non-sterile conditions, preservatives are used to prevent the growth of microbes. A sufficient quantity of one or more preservatives is added so that the emulsified cosmetic composition withstands the growth of bacteria from an experimental inoculation for at least three months.

The emulsified composition can be prepared with propylene glycol, trisodium EDTA, a commercially obtained composition known as Phenonip, and a preservation complex. The preservation complex is a white, colorless, crystalline powder. As shown in Table 2, it contains methylparaben, propylparaben, 2-Bromo-2-Nitropropane-1,3-Diol, and hexamidine isethionate.

Phenonip is a practically colorless viscous liquid mixture of phenoxyethanol, methylparaben, ethylparaben, propylparaben, and butylparaben available from Nipa Laboratories, Inc., Wilmington, Del.

Antioxidants

Because the emulsified cosmetic composition is applied to the skin, it is essential to a consumer that the composition's appearance and odor be pleasing. To maintain the composition's color and prevent malodorous developments, an antioxidant is included in the cosmetic composition. Two antioxidants can be used in the cosmetic composition: Tenox II and ascorbyl palmitate. Tenox II is obtained from Eastman Chemical Products, Inc., Kingsport, Tenn. and contains propylene glycol, butylated hydroxyanisole, propyl gallate, and citric acid.

Emulsifiers

Emulsifiers serve two functions in the present invention. They act like an emulsifier to combine the water soluble and non-water soluble phases together; that is, form a stable bridge between the waters and the oils of the ingredients. The emulsifiers also serve as emollients, providing a pleasant, aesthetically appropriate, tactile feeling when the emulsified composition is applied to the skin.

The preferred cosmetic composition comprises the emulsifiers identified in Table 1, namely isodecyl oleate, C12-15 alcohols benzoate, arachidyl propionate, octyldodecyl stearoyl stearate, steareth-2, PEG-8 stearate, isoceteth-20, steareth-21, acetylated lanolin, dimethicone and 3-cyclohexene-1-methanol $\alpha$, 4-dimethyl-$\alpha$(4-methyl-3-pentenyl) (hereinafter "bisabolol").

Thickener

Preferably the composition contains sufficient thickener that the cosmetic composition does not run off the face and other skin areas when applied. The thickeners complement the function of the emulsifiers in holding together the water and oil phases of the composition. The emulsified composition preferably employs as thickeners xanthan gum and carrageenan.

Emulsified base

Demineralized water is preferably used in the cosmetic composition as the emulsified base.

Colorant

The cosmetic composition can include at least one colorant, preferably titanium dioxide.

Preparation of Cosmetic Composition

In the preparation of the composition, it is important not to denature the protein components. However, in order to make a uniform dispersion, it is necessary to heat many of the ingredients. Accordingly, the protein-containing ingredients are combined with the heated ingredients only after the heated ingredients have been cooled to a temperature of less than 50° C.

Referring to Table 4, a first mixture is formed by dispersing Trisodium EDTA and the preservation complex in water at about 80° C. to about 90° C. A separate second mixture is formed by heating and melting the emulsifiers, antioxidants, and sunscreens at about 80° C to about 90° C. The second mixture is then added to the first mixture to form a blend. To the blend there is added a first slurry of thickeners comprising xanthan gum and carrageenan dispersed in propylene glycol. A colorant, titanium dioxide, is then added to the blend.

The protein-containing components, namely the Iconoderm and Flavoplasmine are dispersed at about room temperature in a portion of the water, and to this dispersion there is added a second slurry of thickeners dispersed in propylene glycol to form a protein-containing gel.

The protein-containing gel is added to the blend containing the colorant only after the blend is cooled to a temperature of less than about 50° C. The remaining ingredients, namely the Phenonip preservative and the fragrance, if any, are added to form the cosmetic composition.

TABLE 1

CONCENTRATION OF INGREDIENTS IN THE COSMETIC COMPOSITION

| Ingredient | Concentration (% by weight of total composition) | |
|---|---|---|
| | Preferred | Range (Approx.) |
| ANTI-AGING AND ANTI-FREE RADICAL | | |
| Iconoderm LS 1054B (1) | 4 | 3.4–4.6 |

TABLE 1-continued
CONCENTRATION OF INGREDIENTS IN THE COSMETIC COMPOSITION

| Ingredient | Concentration (% by weight of total composition) | |
|---|---|---|
| | Preferred | Range (Approx.) |
| Flavoplasmine LS 2704P2 (1) | 10 | 8.5–11.5 |
| PRESERVATIVES | | |
| Trisodium EDTA | 0.05 | 0.04–0.06 |
| Preservation Complex (1) | 0.35 | 0.3–0.4 |
| Phenonip (1) | 1 | 0.8–1.2 |
| THICKENERS | | |
| Xanthan Gum | 0.4 | 0.3–0.5 |
| Carrageenan | 0.5 | 0.4–0.6 |
| ANTI-OXIDANTS | | |
| TENOX II (1) | 0.1 | 0.08–0.11 |
| Ascorbyl Palmitate | 0.02 | 0.01–0.03 |
| Emulsifiers | | |
| Isodecyl Oleate | 1.5 | 1.3–1.7 |
| C12-15 Alcohols Benzoate | 2 | 1.7–2.3 |
| Arachidyl Propionate | 0.5 | 0.4–0.6 |
| 2-Octyldodecyl-12-Stearoyl Stearate | 0.5 | 0.4–0.6 |
| Steareth-2 (3) | 1.5 | 1.3–1.7 |
| PEG-8 Stearate (4) | 1.5 | 1.3–1.7 |
| Isoceteth-20 (5) | 0.5 | 0.4–0.6 |
| Steareth-21 (6) | 1 | 0.8–1.2 |
| Acetylated Lanolin | 0.5 | 0.4–0.6 |
| Bisabolol (7) | 0.5 | 0.4–0.6 |
| Dimethicone. 100 CS | 0.5 | 0.4–0.6 |
| SOLVENTS | | |
| Demineralized Water (1) | 56 | 47–64 |
| Propylene Glycol (2) | 6 | 5–7 |
| SUNSCREENS | | |
| Octyldimethyl PABA (8) | 7 | 6–8 |
| Benzophenone-3 (9) | 3 | 2.5–3.5 |
| COLORANT | | |
| Titanium Dioxide | 0.5 | 0.4–0.6 |
| FRAGRANCE | 0.7 | |

(1) See Table 2 for detailed composition
(2) Also serves as a preservative
(3) Polyoxyethylene (2) stearylether with 0.01% butylated hydroxyanisole and 0.005% citric acid.
(4) Polyoxyethylene 8 monostearate-polyethylene glycol ester of stearic acid.
(5) Polyethylene glycol ether of isocetyl alcohol
(6) Polyoxyethylene (26) stearylether with 0.01% butylated hydroxyanisole and 0.005% citric acid.
(7) 3-cycloherene-1-methanol. α, 4-dimethyl-α-(4-methyl-3-pentenyl)
(8) 2-ethyl hexyl p-dimethyllamino benzoate
(9) 2-hydroxy-4-methoxy benzophenone

TABLE 2
INGREDIENTS IN ICONODERM, FLAVOPLASMINE, STABILIZE LS 207B, TENOX II AND PHENONIP

| Ingredient | Concentration (% by weight of total composition) | |
|---|---|---|
| | Preferred | Possible Range |
| Iconoderm LS 1054B | | |
| Serum Proteins | 25% | 21–28% |
| Hydrolyzed Animal Protein | 26% | 22–30% |
| Glycogen | 5% | 4–6% |
| Sodium Lactate | 7% | 6–8% |
| Sodium Pyrrolidone Carboxylate | 7% | 25–35% |
| Flavoplasmine LS 2704P2 | | |
| Butcher Broom Extract | 10% | 8.5–11.5% |
| Buckwheat Extract | 10% | 8.5–11.5% |
| Passion Flower Extract | 10% | 8.5–11.5% |
| Serum Proteins | 10% | 8.5–11.5% |
| PEG 6-32 (1) | 7% | 6–8% |
| Hydrolyzed Animal Protein | 3.5% | 3–4 |
| Glycogen | 1% | 0.8–1.2% |
| Glycerin | 48.5% | 41–55% |
| Preservation Complex | | |
| Methylparaben | 75% | 64–89% |
| Propylparaben | 5% | 4–6% |
| 2-Bromo-2-Nitropropane-1,3-Diol | 10% | 8.5–11.5% |
| Hexamidine isethionate | 10% | 8.5–11.5 |
| Tenox II | | |

TABLE 2-continued
INGREDIENTS IN ICONODERM, FLAVOPLASMINE, STABILIZE LS 207B, TENOX II AND PHENONIP

| Ingredient | Concentration (% by weight of total composition) | |
|---|---|---|
| | Preferred | Possible Range |
| Propylene Glycol | 70% | 60–80% |
| Butylated Hydroxyanisole | 20% | 17–23% |
| Propyl Gallate | 6% | 5–7% |
| Citric Acid | 4% | 3–5% |
| Phenonip | | |
| Phenoxyethanol | 70% | 60–80% |
| Methylparaben | 15% | 13–17% |
| Ethylparaben | 5% | 4–6% |
| Propylparaben | 5% | 4–6% |
| Butylparaben | 5% | 4–6% |

(1) polyoxyethylene 6 monostearate-polyethylene glycol ester of stearic acid

TABLE 3
SUNSCREEN INGREDIENTS

Aminobenzoic Acid
Cinoxate
Diethanalamine p-Methoxycinnamate
Digalloyl Trioleate
Dioxybenzone
Ethyl 4-[bis[hydroxypropyl] Aminobenzoate
2-Ethylhexyl 2-Cyano-3,3-diphenylacrylate
Ethylhexyl p-methoxycinnamate
2-Ethyhexyl Salicylate
Glyceryl Aminobenzoate
Homosalate
Lawsone with Dyhydroxyacetone
Menthyl Anthranilate
Oxybenzone
Padimate A
Padimate O
2-Phenylbenzimidazole-5-Sulfonic Acid
Red Petrolatum
Suiisobenzone
Titanium Dioxide
Triethanolamine Salicylate

Clinical studies

Tests with the composition of Table 1 revealed that a three-week treatment with the cosmetic composition improved skin color for dry, aged, and scaling skin. Moreover, skin color became less red, clearer, brighter, more brilliant, more lively looking, and more colorful. These results were particularly significant with dry and aged skin.

Although the present invention has been described with reference to a certain version thereof, other versions are possible. Therefore, the spirit and scope of the appended claims should not be limited to the preferred version contained herein.

TABLE 4
METHOD OF PREPARATION OF COSMETIC COMPOSITION

| Ingredient | Concentration (% by weight of total composition) |
|---|---|
| BLEND | |
| First Mixture | |
| Demineralized Water | 40.41 |
| Trisodium EDTA | 0.05 |
| Preservation Complex | 0.35 |
| Second Mixture | |
| Isodecyl Oleate | 1.5 |
| C12-15 Alcohols Benzoate | 2.0 |
| Arachidyl Propionate | 0.5 |
| Octyldodecyl Stearoyl Stearate | 0.5 |
| Steareth-2 | 1.5 |

TABLE 4-continued
METHOD OF PREPARATION OF COSMETIC COMPOSITION

| Ingredient | Concentration (% by weight of total composition) |
|---|---|
| PEG-8 Stearate | 1.5 |
| Isoceteth-20 | 0.5 |
| Steareth-21 | 1.0 |
| Tenox 11 | 0.1 |
| Ascorbyl Palmitate | 0.02 |
| Octyldimethyl PABA | 7.0 |
| Benzophenone-3 | 3.0 |
| Acetylated Lanolin | 0.5 |
| Bisabolol | 0.5 |
| Dimethicone | 0.5 |
| *First Slurry of Thickeners* | |
| Xanthan Gum | 0.35 |
| Carrageenan | 0.35 |
| Propylene Glycol | 4.0 |
| *Colorant* | |
| Titanium Dioxide in | 0.5 |
| Demineralized Water | 5.0 |
| *Preservative* | |
| Phenonip | 1.0 |
| Fragrance | 0.7 |
| *PROTEIN-CONTAINING GEL* | |
| Demineralized Water | 10.0 |
| Iconoderm | 4.0 |
| Flavoplasmine | 10.0 |
| *Second Slurry of Thickeners* | |
| Xanthan Gum | 0.05 |
| Carrageenan | 0.15 |
| Propylene Glycol | 2.0 |

What is claimed is:

1. An emulsified cosmetic composition for retarding the effects of aging on the complexion of the skin comprising:
water, and emulsified and dispersed in the water,
(a) an anti-aging agent for retarding the effects of natural aging on the complexion of the skin, including deterioration of the complexion of the skin from free radical activity;
(b) a sunscreen for retarding the effects of aging from sunlight on the complexion of the skin;
(c) a preservative for preventing microbial growth in the composition;
(d) a thickener to increase the viscosity of the composition;
(e) an anti-oxidant; and
(f) an emulsifier.

2. The cosmetic composition of claim 1 wherein the anti-aging agent is selected from the group consisting of proteins, flavonoid compounds, glycogen, and combinations thereof.

3. The cosmetic composition of claim 2 wherein the proteins comprise serum proteins and hydrolyzed animal proteins.

4. The cosmetic composition of claim 1 wherein the anti-aging agent comprises from about 1 to about 3 parts by weight serum proteins and from about 0.8 to about 1.2 parts by weight hydrolyzed animal proteins per 100 parts by weight cosmetic composition.

5. The cosmetic composition of claim 2 wherein the flavonoid compounds are provided by plant extracts.

6. The cosmetic composition of claim 5 wherein the plant extracts are selected from the group consisting of butcher broom extract, buckwheat extract, passion flower extract, and combinations thereof.

7. The cosmetic composition of claim 1 wherein the anti-aging agent comprises from about 0.8 to about 1.2 parts by weight butcher broom extract, from about 0.8 to about 1.2 parts by weight buckwheat extract, and from about 0.8 to about 1.2 parts by weight passion flower extract per 100 parts by weight cosmetic composition.

8. The cosmetic composition of claim 1 in which the sunscreen is selected from the group consisting of paraminobenzoic acid derivatives, oxyphenones, benzophenones, titanium dioxide, zinc oxide, cinnamates, and combinations thereof.

9. The composition of claim 1 wherein the sunscreen comprises from about 5 parts to about 9 parts 2ethyl hexyl p-dimethyl amino benzoate and from about 2 parts to about 4 parts 2-hydroxy-4-methoxy benzophenone per 100 parts by weight cosmetic composition.

10. The cosmetic composition of claim 1 in which the anti-aging agent comprises butcher broom extract, buckwheat extract, passion flower extract, serum proteins, hydrolyzed animal proteins and glycogen.

11. An emulsified cosmetic composition intended for the treatment of skin comprising, dispersed in water, glycerin, propylene glycol, C12-15 alcohols benzoate, serum proteins, isodecyl oleate, polyoxyethylene (2) stearylether with 0.01% butylated hydroxyanisole and 0.005% citric acid, polyoxyethylene 8 monostearate-polyethylene glycol ester of stearic acid, hydrolyzed animal protein, polyoxyethylene (26) stearylether with 0.01% butylated hydroxyanisole and 0.005% citric acid, butcher broom extract, buckwheat extract, passion flower extract, fragrance, polyoxyethylene 6 monostearatepolyethylene glycol ester of stearic acid, 2-octyl-dodecyl-12stearoyl stearate, arachidyl propionate, polyethylene glycol ether of isocetyl alcohol, 2-hydroxy-4-methoxy benzophenone, 2-ethyl hexyl p-dimethyllaminoe benzoate, acetylated lanolin, bisabolol, dimethicone, titanium dioxide, carrageenan, sodium lactate, sodium pyrrolidone carboxylate, xanthan gum, glycogen, trisodium EDTA, butylated hydroxyanisole, ascorbyl palmitate, propyl gallate, citric acid, phenoxyethanol, methylparaben, propylparaben, butylparaben, ethylparaben, hexamidine isethionate, and 2-bromo-2-nitropropane-1,3 diol.

12. A method to retard the effects of aging in the skin's complexion comprising the step of applying to the skin the cosmetic composition of claim 1.

13. The cosmetic composition of claim 1 wherein the anti-aging agent for retarding the deterioration of the complexion of the skin from free radical activity is an anti-free radical ingredient selected from the group consisting of vitamins C and E, selenium metal compounds, beta carotene compounds, and derivatives and combinations thereof.

14. An emulsified cosmetic composition for retarding the effects of aging on the complexion of the skin comprising:
water, and emulsified and dispersed in the water,
(a) an anti-aging agent for retarding the effects of natural aging on the complexion of the skin, including deterioration of the complexion of the skin from free radical activity, the anti-aging agent comprising from about 1 to about 3 parts by weight serum proteins, and from about 0.8 to about 1.2 parts by weight hydrolyzed animal proteins per 100 parts by weight cosmetic composition;
(b) a sunscreen for retarding the effects of aging from sunlight on the complexion of the skin;

(c) a preservative for preventing microbial growth in the composition;

(d) a thickener to increase the viscosity of the composition;

(e) an anti-oxidant; and (f) an emulsifier.

15. The cosmetic composition of claim 14 wherein the anti-aging agent for retarding the deterioration of the complexion of the skin from free radical activity is an anti-free radical ingredient selected from the group consisting of vitamins C and E, selenium metal compounds, beta carotene compounds, and derivatives and combinations thereof.

16. A method for retarding the effects of aging in the skin's complexion comprising the step of applying to the skin the cosmetic composition of claim 13.

17. The method of claim 13 wherein the cosmetic composition is applied daily too the skin over a period of at least 3 weeks in length.

18. A method to retard the effects of aging in the skin's complexion comprising the step of applying to the skin the cosmetic composition of claim 11.

* * * * *